(12) United States Patent
Lim et al.

(10) Patent No.: US 10,307,119 B2
(45) Date of Patent: Jun. 4, 2019

(54) MEDICAL IMAGING SYSTEM AND OPERATION METHOD THEREFOR

(71) Applicants: VATECH Co., Ltd., Gyeonggi-do (KR); VATECH EWOO Holdings Co., Ltd., Gyeonggi-do (KR)

(72) Inventors: Hyung Keun Lim, Gyeonggi-do (KR); Jin Pyo Chun, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 128 days.

(21) Appl. No.: 15/125,580

(22) PCT Filed: Mar. 12, 2015

(86) PCT No.: PCT/KR2015/002384
§ 371 (c)(1),
(2) Date: Sep. 12, 2016

(87) PCT Pub. No.: WO2015/137741
PCT Pub. Date: Sep. 17, 2015

(65) Prior Publication Data
US 2017/0000432 A1    Jan. 5, 2017

(30) Foreign Application Priority Data
Mar. 12, 2014   (KR) .................. 10-2014-0029120

(51) Int. Cl.
*A61B 6/00*    (2006.01)
*A61B 6/10*    (2006.01)
(Continued)

(52) U.S. Cl.
CPC .......... *A61B 6/4417* (2013.01); *A61B 3/0091* (2013.01); *A61B 3/113* (2013.01);
(Continued)

(58) Field of Classification Search
CPC ..... A61B 3/0091; A61B 3/113; A61B 5/0077; A61B 6/032; A61B 6/10; A61B 6/14;
(Continued)

(56) References Cited

U.S. PATENT DOCUMENTS

2004/0197727 A1* 10/2004 Sachdeva ................. A61C 7/00
433/24
2009/0092948 A1    4/2009 Gantes
(Continued)

FOREIGN PATENT DOCUMENTS

| JP | 2001-017410 A | 1/2001 |
|---|---|---|
| JP | 2003-030634 A | 1/2003 |
| KR | 10-2006-0077549 A | 7/2006 |
| KR | 10-2011-0006984 A | 1/2011 |
| KR | 10-2013-0028057 A | 3/2013 |

OTHER PUBLICATIONS

European Patent Office, European Search Report of corresponding EP Patent Application No. 15761693.9, dated Nov. 28, 2017.

*Primary Examiner* — George Manuel
(74) *Attorney, Agent, or Firm* — IP Legal Services, LLC

(57) ABSTRACT

The purpose of the present invention is to provide a method for obtaining a more effective 3D facial image for medical use. The present invention provides a medical imaging system includes a 2D surface image obtaining device including at least one camera for photographing a plurality of 2D facial images of an examinee, at different photography angles or ranges, a visual guidance configured to fix an examinee's line of vision, an X-ray radiography device for radiographing a 3D X-ray radiograph of the examinee's head, and an image synthesis unit for generating a 3D facial image by matching the plurality of 2D facial images with the 3D X-ray radiograph.

8 Claims, 4 Drawing Sheets

(51) Int. Cl.
    *A61B 6/14*     (2006.01)
    *A61B 3/113*    (2006.01)
    *A61B 3/00*     (2006.01)
    *A61B 5/00*     (2006.01)
    *A61B 6/03*     (2006.01)

(52) U.S. Cl.
    CPC ............ *A61B 5/0077* (2013.01); *A61B 6/032* (2013.01); *A61B 6/10* (2013.01); *A61B 6/14* (2013.01); *A61B 6/4429* (2013.01); *A61B 6/501* (2013.01); *A61B 6/5247* (2013.01)

(58) Field of Classification Search
    CPC ..... A61B 6/4417; A61B 6/4429; A61B 6/501; A61B 6/5247
    See application file for complete search history.

(56) References Cited

U.S. PATENT DOCUMENTS

| | | |
|---|---|---|
| 2010/0036233 A1 | 2/2010 | Zhu et al. |
| 2010/0172567 A1* | 7/2010 | Prokoski ............ A61B 5/0064 |
| | | 382/132 |
| 2010/0255445 A1 | 10/2010 | Gantes |
| 2011/0245951 A1 | 10/2011 | Gantes |
| 2011/0256508 A1 | 10/2011 | Gantes |
| 2012/0046668 A1 | 2/2012 | Gantes |
| 2012/0156638 A1 | 6/2012 | Gantes |
| 2012/0300895 A1 | 11/2012 | Koivisto et al. |
| 2012/0300900 A1 | 11/2012 | Koivisto et al. |
| 2016/0157970 A1 | 6/2016 | Gantes |
| 2016/0174916 A1 | 6/2016 | Nyholm et al. |
| 2017/0095294 A1 | 4/2017 | Gantes |

* cited by examiner

MEDICAL IMAGING SYSTEM AND OPERATION METHOD THEREFOR

CROSS REFERENCE TO RELATED APPLICATIONS

This application is a National Stage Patent Application of PCT International Patent Application No. PCT/KR2015/002384 (filed on Mar. 12, 2015) under 35 U.S.C. § 371, which claims priority to Korean Patent Application No. 10-2014-0029120 (filed on Mar. 12, 2014), the teachings of which are incorporated herein in their entireties by reference.

TECHNICAL FIELD

The present invention relates generally to a medical imaging system. More particularly, the present invention relates to a medical imaging system capable of efficiently obtaining a medical 3D facial image and an operation method therefor.

BACKGROUND ART

In general, in the medical field, an X-ray radiograph, such as computed tomography (CT), is used for a diagnosis.

However, since the X-ray radiograph illustrates an inside of a human body, an ordinary person is not accustomed to the X-ray radiograph except for a trained professional such as a doctor.

Especially, in the dental or plastic surgery field, use of only the X-ray radiograph cannot satisfy demand for easily identifying a facial change after treatment.

In this aspect, a way to efficiently obtain a 3D facial image for 3-dimensionally illustrating a part of a human body, such as a face, is required.

In this regard, it may be considered to use a three dimensional (3D) imaging device commonly used for 3D movies. However, it is problematic in that the 3D imaging device is very expensive, and takes much time for 3D scanning.

Accordingly, a way to obtain a more effective 3D facial image for medical use is urgently required.

DISCLOSURE

Technical Problem

Accordingly, the present invention has been made keeping in mind the above problems occurring in the related art, and the present invention is intended to provide a technique capable of obtaining a more effective 3D facial image for medical use.

Technical Solution

In order to accomplish the above object, the present invention provides a medical imaging system, the system including: a two dimensional (2D) image obtaining device including at least one camera photographing a plurality of 2D facial images of an examinee, the plurality of 2D facial images having different photography angles and ranges; an X-ray radiography device radiographing a 3D X-ray radiograph of the examinee's head; and an image synthesis unit generating a 3D facial image by matching the plurality of 2D facial images with the 3D X-ray radiograph.

In another aspect of the present invention, there is provided a medical imaging system, the system including: a 2D image obtaining device including at least one camera photographing a plurality of 2D facial images of an examinee, the plurality of 2D facial images having different photography ranges; an X-ray radiography device radiographing a 3D X-ray radiograph of the examinee's head; and an image synthesis unit generating a 3D facial image by matching the plurality of 2D facial images with the 3D X-ray radiograph.

Here, the at least one camera may comprise a single camera, the single camera obtaining the plurality of 2D facial images depending on movement of the single camera. The at least one camera may comprise a plurality of cameras located at different positions. The 2D image obtaining device may be located in front of the examinee, and may include a visual guidance fixing an examinee's line of vision. The 2D image obtaining device may be located in front of the examinee, and may include a vision sensing means for sensing an examinee's line of vision. The 2D image obtaining device may further include a visual guidance fixing the examinee's line of vision. The vision sensing means may be configured to sense the examinee's line of vision until photography of the plurality of 2D facial images is completed.

In another aspect of the present invention, there is provided an operation method for a medical imaging system, the operation method including: photographing a plurality of 2D facial images of an examinee by using at least one camera, the plurality of 2D facial images having different photography ranges; radiographing a 3D X-ray radiograph of the examinee's head; and generating a 3D facial image by matching the plurality of 2D facial images with the 3D X-ray radiograph.

Here, when an examinee's line of vision is fixed to a vision drawing means located in front of the examinee, the plurality of 2D facial images of the examinee may be photographed by using the at least one camera, the plurality of 2D facial images having different photography ranges.

In another aspect of the present invention, there is provided an operation method for a medical imaging system, the operation method including: photographing a plurality of 2D facial images of an examinee by using at least one camera, the plurality of 2D facial images having different photography ranges; radiographing a 3D X-ray radiograph of the examinee's head; and generating a 3D facial image by matching the plurality of 2D facial images with the 3D X-ray radiograph.

Here, when it is sensed by a vision sensing means that an examinee's line of vision is fixed to a preset position, the plurality of 2D facial images of the examinee may be photographed by using the at least one camera at different photography ranges. The vision sensing means may be configured to sense the examinee's line of vision until the photographing of the plurality of 2D facial images is completed.

Advantageous Effects

According to the present invention, a 3D surface image can be obtained by using a process of capturing a plurality of 2D surface images with a conventional camera and synthesizing the plurality of 2D surface images a with a 3D X-ray image. Thus, a 3D surface image can be obtained without using a separate 3D imaging device. Accordingly, costs and time for generating the 3D surface image can be reduced, and efficiency can be increased.

Furthermore, since a vision drawing means is provided for fixing a vision of an examinee during the photography by a camera, accuracy and reliability of a 3D surface image is obtained and psychological discomfort of an examinee can be relived.

Furthermore, The accuracy and reliability of the 3D surface image, and psychological discomfort of an examinee can be more improved by using a vision sensing means for sensing an examinee's line of vision.

Further, the convenience of the system in use can be improved.

MODE FOR INVENTION

Herein below, exemplary embodiments of the present invention will be described in detail with reference to the accompanying drawings.

Figure 1:
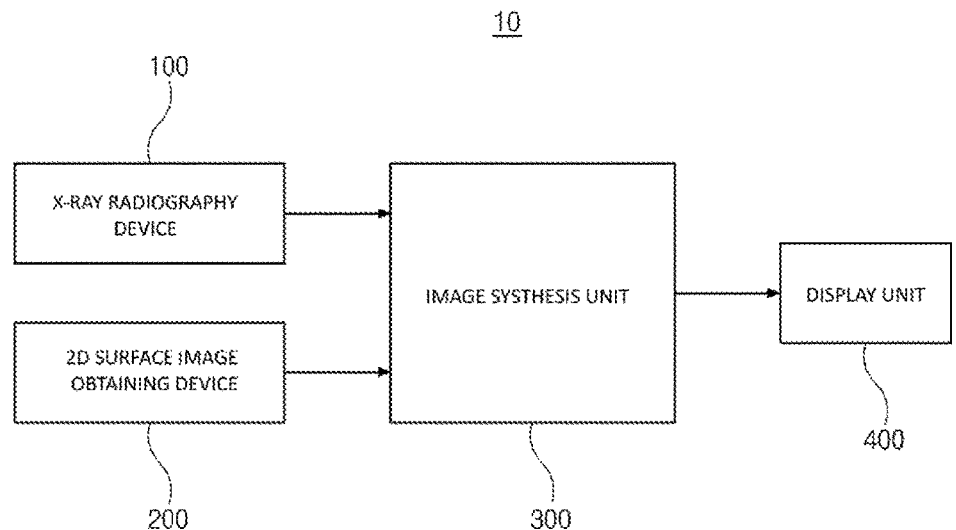
FIG. 1 is a schematic block diagram illustrating a configuration of a medical imaging system according to a first embodiment of the present invention.
Figure 2:
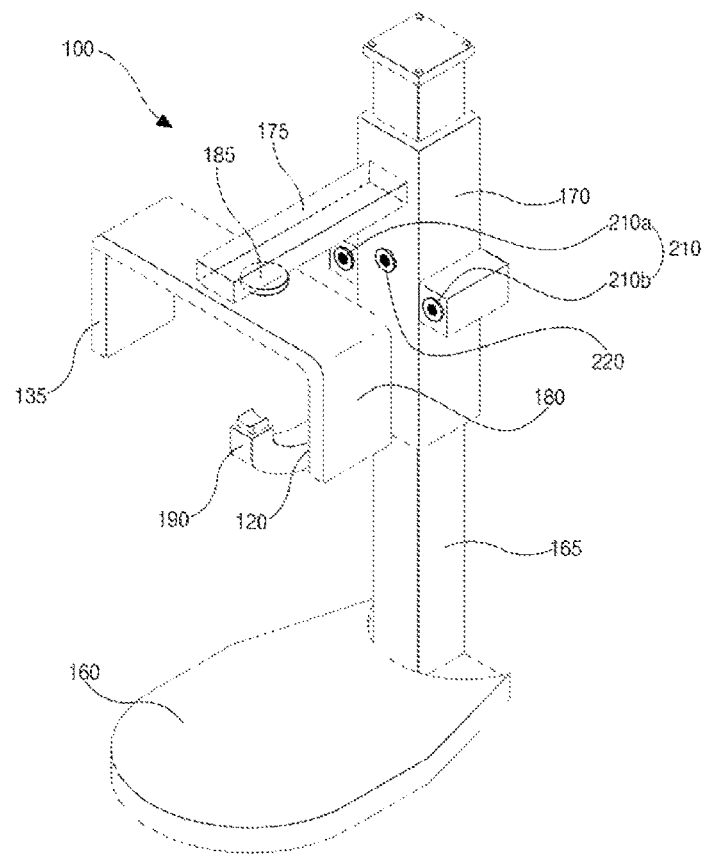
FIG. 2 is a schematic view illustrating an example of an X-ray radiography device and a 2D surface image obtaining device of the medical imaging system according to the first embodiment of the present invention.
Figure 3:
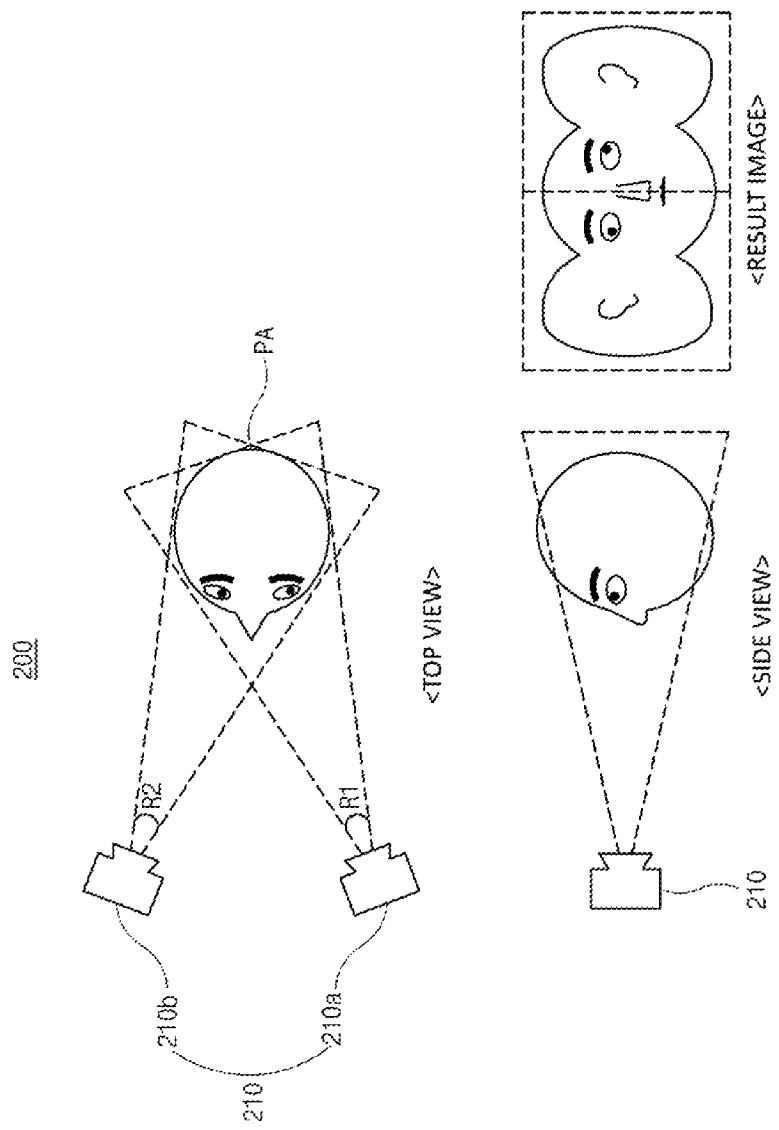
FIG. 3 is a schematic view illustrating a photography process performed using the 2D surface image obtaining device of the medical imaging system according to the first embodiment of the present invention.

FIG. 1 is a schematic block diagram illustrating a configuration of a medical imaging system according to a first embodiment of the present invention, FIG. 2 is a schematic view illustrating an example of an X-ray radiography device and a 2D surface image obtaining device of the medical imaging system according to the first embodiment of the present invention, and FIG. 3 is a schematic view illustrating a photography performed using the 2D surface image obtaining device of the medical imaging system according to the first embodiment of the present invention.

The medical imaging system 10 according to the first embodiment of the present invention is configured to form a 3D surface image by synthesizing 2D surface images with a 3D X-ray radiograph. For convenience, in the embodiments of the present invention, the medical imaging system for generating a facial image is described.

Referring to FIG. 1, the medical imaging system 10 according to the embodiments of the present invention may include the X-ray radiography device 100, the 2D surface image obtaining device 200, an image synthesis unit 300, and a display unit 400.

The X-ray radiography device 100 is configured to obtain a 3D X-ray radiograph of an examinee PA, for example, an 3D X-ray radiograph of the examinee's head. As an example, a device for dental computed tomography (CT) may be utilized, but not limited thereto.

The X-ray radiography device 100 is described with reference to FIG. 2. The X-ray radiography device 100 may include: a base 160 by which the X-ray radiography device 100 is placed on and fixed to the ground; a support column 165 connected to the base 160 and extending from the base in a direction perpendicular to the ground; an elevating and lowering member 170 vertically elevating and lowering along the support column 165; a rotating arm supporting member 175 connected to an upper portion of the elevating and lowering member 170 and extending from the upper portion of the elevating and lowering member 170 in a direction parallel to the ground; a rotating arm 180 connected to a lower surface of the rotating arm supporting member 175 and operated by a rotating arm operating means 185; and an X-ray radiation unit 120 and a sensor 135 located at respective opposite ends of the rotating arm 180 in a state of being faced each other for X-ray radiography, such as panorama or computed tomography (CT).

Alternatively, the X-ray radiography device 100 may be configured as a wall-hanging shape without the base 160 in such a way that the support column 165 is attached to a wall.

Meanwhile, a chin supporting member 190 connected to the elevating and lowering member 170 may be disposed between the X-ray radiation unit 120 and the sensor 135. Further, the chin supporting member 190 supports the examinee's chin during the computed tomography (CT) or panorama radiography.

The rotating arm 180 may horizontally move in a direction parallel to the ground or rotate based on a rotational shaft perpendicular to the ground by using the rotating arm operating means 185.

The 3D X-ray image radiographed by the above-described X-ray radiography device 100 may be transmitted to the image synthesis unit 300.

The 2D surface image obtaining device 200 may obtain 2D facial images of the examinee PA. Especially, it is desirable that the 2D surface image obtaining device 200 is configured to obtain a plurality of 2D facial images having different photography angles and ranges from each other. In this case, the plurality of 2D facial images may be transmitted to the image synthesis unit 300.

The image synthesis unit 300 matches and combines the 3D X-ray image of the examinee PA transmitted from the X-ray radiography device 100 with the plurality of 2D facial images transmitted from the 2D surface image obtaining device 200. Accordingly, the image synthesis unit 300 may obtain a 3D facial image in which the plurality of 2D facial images is matched with the 3D X-ray radiograph.

The display unit 400 displays the 3D facial image obtained by the image synthesis unit 300. Thus, a facial change by dental treatment may be easily identified based on the 3D facial image.

Hereinafter, the 2D surface image obtaining device 200 is described in more detail.

Referring to FIGS. 2 and 3, the 2D surface image obtaining device 200 may include cameras 210.

The cameras 210 are configured to photograph the 2D facial images of the examinee PA, and conventional cameras may be utilized as the cameras 210.

Here, it is desirable that the 2D surface image obtaining device 200 obtains at least two facial images at each of different photography angles and in each of different photography ranges. For convenience, in the embodiments of the present invention, two facial images are obtained and are symmetrical to each other based on the middle line of the examinee's face.

In this case, when the two facial images are obtained, at least one camera 210 may be utilized. For convenience, in the embodiments of the present invention, first and second cameras 210a and 210b are utilized.

The first and second cameras 210a and 210b may be located to be symmetrical to each other based on a front direction of the examinee PA, and may have the same angle of view. In this case, as shown in FIG. 2, the first and second cameras 210a and 210b may be disposed in the X-ray radiography device 100, for example, at opposite sides of the elevating and lowering member 170, but not limited thereto.

As described, first and second facial images having photography ranges R1 and R2 symmetrical to each other may be obtained by the first and second cameras 210a and 210b located to be symmetrical to each other.

In this case, when an angle of a front direction of the examinee's face is 0° and angles of left and right directions of the examinee's face are ±90°, respectively, the first camera is located within a range of greater than 0° and less than 90° and the second camera is located within a range of less than 0° and greater than −90° in a state of being symmetrical to each other. Preferably, the first camera is located within a range of greater than 20° and less than 70° and the second camera is located within a range of less than −20° and greater than −70° in a state of being symmetrical to each other. Thus, the face of the examinee PA is photographed by each of the first and second cameras. Accordingly, the first and second facial images reflect front, left, and right shapes of the examinee's face. Thus, when the first and second facial images are matched with the 3D X-ray image that is described later, the 3D facial image that is more approximate to a real face shape of the examinee may be obtained.

Meanwhile, when a single camera 210 is utilized, the single camera 210 may obtain first and second facial images by photography in the positions of the first and second cameras 210a and 210b.

As described above, when the two 2D facial images are obtained by using the first and second cameras 210a and 210b, minor time difference in photography may be generated. That is, shooting time of the first camera 210a and shooting time of the second camera 210b are different from each other due to various factors.

Furthermore, when photography is performed by movement of the single camera 210, time difference in photography is inevitable.

As described, when time difference in photography is happened, focuses of the examinee's line of visions of the first and second facial images may differ from each other, and the examinee's face positions of the first and second facial images may differ from each other.

In this case, a 3D facial image obtained by the combination has low accuracy and reliability. Furthermore, as shown in FIG. 3, when difference between the examinee's line of visions is generated, focuses of left and right eyes of the examinee are different from each other in the 3D facial image due to the difference. Thus, the 3D facial image is awkward and may cause inconvenience to the examinee PA.

Figure 4:
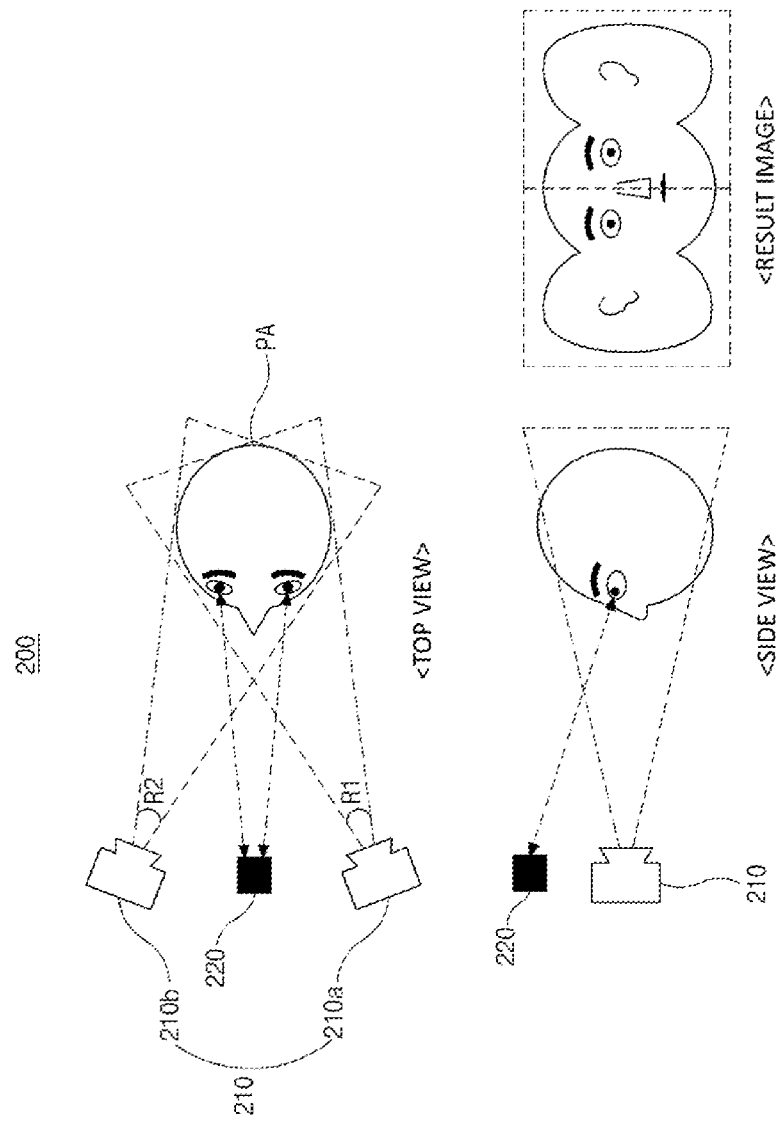
FIG. 4 is a schematic view illustrating a photography process performed using the 2D surface image obtaining device including a vision drawing means of the medical imaging system according to the first embodiment of the present invention.

In order to overcome the above problem, as shown in FIGS. 2 and 4, a visual guidance 220 may be provided as a target for fixing the examinee's line of vision. In this case, as shown in FIG. 2, the visual guidance 220 may be disposed in the X-ray radiography device 100, for example, on the front surface of the elevating and lowering member 170 located between the first and second cameras 210a and 210b, but not limited thereto.

In this case, a marker or light emitting diode (LED) having high visibility may be utilized as the visual guidance 220 for the examinee PA, but not limited thereto.

The visual guidance 220 is located in front of the examinee PA. Preferably, the visual guidance 220 is located on the symmetry axis between the first and second cameras 210a and 210b.

Therefore, since the visual guidance 220 is utilized, the examinee's face may continue to be fixed during the photography by the camera 210 in such a way that the examinee PA gazes at the visual guidance 220.

Accordingly, when time difference in photography is obtained between the 2D facial images, as shown in FIG. 4, the examinee's line of vision and face position are prevented from being changed. Thus, it is possible to obtain a 3D facial image having high accuracy and reliability without causing inconvenience to the examinee PA.

Meanwhile, the photography of the camera 210 may be manually performed by a user.

Meanwhile, the medical imaging system 10 according to the present invention may include an audio output means, such as a speaker. In this case, a guide message, for example, "Look in front of you", is output from the audio output means so as to instruct the examinee PA to gaze at the the visual guidance 220. Thereafter, after a preset time elapses, the photography of the camera 210 is performed.

As described, according to the embodiment of the present invention, the 3D facial image is obtained by matching the plurality of 2D facial images photographed by the camera 210 with the 3D X-ray image radiographed for a diagnosis.

That is, the 2D facial images are obtained by the camera, and are matched with the 3D X-ray radiograph, thereby obtaining the 3D facial image without using a separate 3D imaging device.

Accordingly, costs and time for generating the 3D facial image may be reduced, thereby increasing efficiency.

Furthermore, since the visual guidance is provided to fix the examinee's line of eyes during the photography using the camera, it is possible to obtain a 3D facial image having high accuracy and reliability without causing inconvenience to the examinee.

Figure 5:
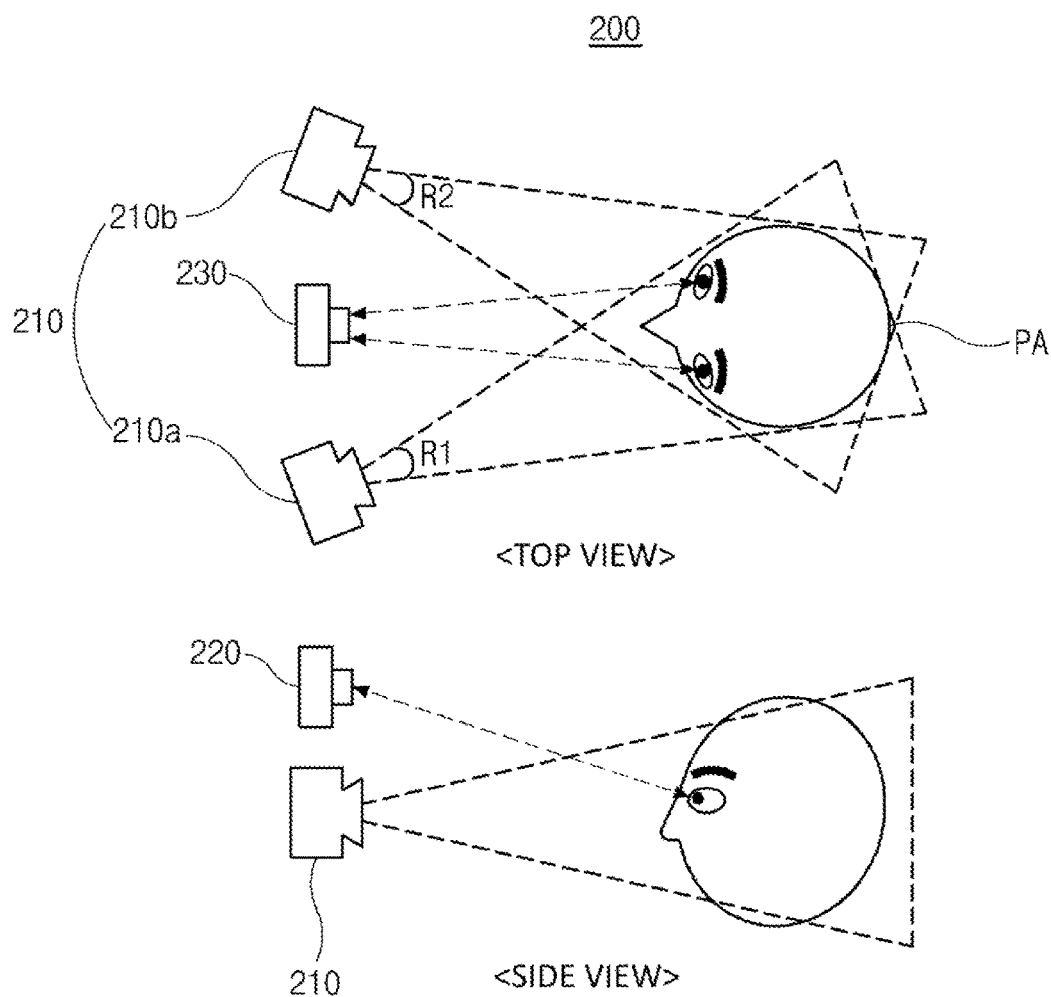
FIG. 5 is a schematic view illustrating a 2D surface image obtaining device of a medical imaging system according to a second embodiment of the present invention.

FIG. 5 is a schematic view illustrating a 2D surface image obtaining device of a medical imaging system according to a second embodiment of the present invention.

For convenience, detailed descriptions of the same configuration as or similar configuration to the medical imaging system according to the first embodiment are omitted.

Referring to FIG. 5, the 2D image obtaining device 200 according to the second embodiment of the present invention may include a vision sensing means 230.

The vision sensing means 230 may include an eye tracking device for tracking positions of the examinee's pupils. The eye tracking device may be configured as a video analysis method of detecting movements of the examinee's pupils by analyzing a real-time video image so as to calculate a direction of the examinee's line of vision based on a fixed position reflected in the examinee's corneas, a contact lens method of using a light reflected in a contact lens including a mirror or using a magnetic field of a contact lens including a coil, and a sensor attachment method of using an electric field depending on movements of the examinee's eyes by attaching a sensor around the examinee's eyes, but not limited thereto.

Furthermore, the vision sensing means 230 may function as the visual guidance 220 according to the first embodiment. That is, the examinee's line of vision may be fixed to the vision sensing means in such a way that the vision sensing means 230 is located in front of the examinee PA. For example, in the similar manner as the visual guidance 220 according to the first embodiment, the vision sensing means 230 may be disposed in the X-ray radiography device 100, for example, in the front surface of the elevating and lowering member 170 located between the first and second cameras 210a and 210b, but not limited thereto.

Meanwhile, the visual guidance 220 according to the first embodiment and the vision sensing means 230 may be provided together.

For example, the vision sensing means 230 is activated by a photography instruction of a user. Further, the vision sensing means 230 may sense the examinee's line of vision by detecting positions of the examinee's pupils.

As a result of sensing the examinee's line of vision, if it is determined that the examinee's line of vision is headed for a preset position, for example, the vision sensing means 230, then a determination result may be transmitted to a control circuit (not shown) for controlling cameras 210.

In response, the control circuit may control the cameras 210 so that the cameras 210 perform photography. Further, at the same time, the control circuit may control the X-ray radiography device 100 so that the X-ray radiography device 100 performs X-ray radiography.

Meanwhile, when the examinee's line of vision departs from the preset position located in front of the examinee PA, a guide message, for example, "Look in front of you", may be output from an audio output means so as to instruct the examinee PA to gaze at the preset position.

When the examinee's line of vision is headed for the preset position according to the guide message, the vision sensing means 230 may sense the examinee's line of vision, and photography may be performed. Of course, at the same time, the X-ray radiography device 100 may be controlled to perform the X-ray radiography.

Meanwhile, it is desirable that the vision sensing means 230 continues to sense the examinee's line of vision until the photography is completed. Thus, when the examinee's line of vision is moved during the photography, the information may be transmitted to the control circuit so as to stop the photography or perform the photography again. For example, when the examinee's line of vision is moved during the photography of the first and second cameras 210a and 210b, the next photography may be stopped or photography may be restarted. In this case, as a result of sensing the examinee's line of vision by the vision sensing means 230, when difference between the examinee's line of visions is minor, the X-ray radiography of the X-ray radiography device 100 may continue, but when the difference between the examinee's line of visions is large, the X-ray radiography of the X-ray radiography device 100 may stop.

Furthermore, it may be noted to a user via a monitor that the examinee's line of vision is moved.

In this case, when the examinee's line of vision is moved, a guide message, in which the photography has been stopped or will be performed again, may be output. Thereafter, when the examinee's line of vision is headed for the preset position located in front of the examinee PA, the photography may continue in such a way that the vision sensing means 230 senses the examinee's line of vision.

As described, in the second embodiment, it is possible to obtain a 3D facial image having high accuracy and reliability without causing inconvenience to a user by using the vision sensing means 230 for sensing the examinee's line of vision. Furthermore, the convenience of a user using the system may be improved.

In the embodiments, when a plurality of cameras is utilized, two cameras are utilized. Meanwhile, when three cameras are utilized, the three cameras may be located in upper left, upper right, and lower middle positions based on a direction in front of the examinee, respectively. Meanwhile, when four cameras are utilized, the four cameras may be located in upper left, upper right, lower left, and lower right positions based on the direction in front of the examinee, respectively.

As described, according to the embodiments of the present invention, the 2D facial images are obtained by a camera, and the 2D facial images are matched with a 3D X-ray radiograph. Thus, a 3D facial image may be obtained without using a separate 3D imaging device. Accordingly, costs and time for generating the 3D facial image may be reduced, and efficiency may be increased.

Furthermore, since the vision drawing means is used during the photography using a camera, a 3D facial image having high accuracy and reliability can be obtained without causing inconvenience to an examinee.

Furthermore, the present invention can obtain a 3D facial image having high accuracy and reliability without causing inconvenience to a user by using the vision sensing means for sensing the examinee's line of vision. Further, the convenience of a user in using the system can be improved.

The invention claimed is:

1. A medical imaging system, the system comprising:
   a 2D surface image obtaining device including at least one camera for photographing a plurality of 2D facial images of an examinee;
   an X-ray radiography device for radiographing a 3D X-ray radiograph of the examinee's head;
   a visual guidance configured to fix an examinee's line of vision in front of the examinee; and
   an image synthesis unit directly coupled to the 2D surface image obtaining unit and the X-ray radiography device to respectively receive the plurality of 2D facial images and the 3D X-ray radiograph and to generate a 3D facial image by matching the plurality of 2D facial images with the 3D X-ray radiograph.

2. The system of claim 1, wherein said at least one camera photographs examinee at different angles or ranges.

3. The system of claim 1, wherein the at least one camera includes a single camera moving and obtaining the plurality of 2D facial images.

4. The system of claim 1, wherein the at least one camera includes a plurality of cameras located at different positions.

5. The system of claim 1, further comprise:
   a vision sensing means for sensing an examinee's line of vision.

6. The system of claim 5, wherein the vision sensing means is configured to sense the examinee's line of vision until the photographing of the plurality of 2D facial images is completed.

7. The system of claim 1, further comprising:
   a base; and
   a support column attached to the base, wherein the 2D surface image obtaining device and the visual guidance are located on the support column.

8. The system of claim 1, wherein the X-ray radiography device, the 2D surface image obtaining device, and the visual guidance are housed in a self contained system.

* * * * *